United States Patent
Evers et al.

(10) Patent No.: US 10,794,903 B2
(45) Date of Patent: Oct. 6, 2020

(54) PULSED MAGNETIC ACTUATION FOR SENSITIVE ASSAYS

(75) Inventors: Toon Hendrik Evers, Eindhoven (NL); Mikhail Mikhaylovich Ovsyanko, Eindhoven (NL)

(73) Assignee: MINICARE B.V., Eindhoven (NL)

( * ) Notice: Subject to any disclaimer, the term of this patent is extended or adjusted under 35 U.S.C. 154(b) by 1636 days.

(21) Appl. No.: 13/124,426

(22) PCT Filed: Oct. 6, 2009

(86) PCT No.: PCT/IB2009/054374
§ 371 (c)(1),
(2), (4) Date: Jun. 28, 2011

(87) PCT Pub. No.: WO2010/044007
PCT Pub. Date: Apr. 22, 2010

(65) Prior Publication Data
US 2011/0244596 A1    Oct. 6, 2011

(30) Foreign Application Priority Data
Oct. 17, 2008  (EP) ..................... 08166901

(51) Int. Cl.
*G01N 33/543* (2006.01)
*B03C 5/02* (2006.01)
(Continued)

(52) U.S. Cl.
CPC .. *G01N 33/54333* (2013.01); *B01L 3/502761* (2013.01); *B03C 1/288* (2013.01);
(Continued)

(58) Field of Classification Search
CPC .. G01N 35/0098; G01N 27/00; G01N 33/587; G01N 33/54326; G01N 2446/00;
(Continued)

(56) References Cited

U.S. PATENT DOCUMENTS

| | | |
|---|---|---|
| 2003/0012693 A1 | 1/2003 | Otillar |
| 2005/0035757 A1 | 2/2005 | Prins |

(Continued)

FOREIGN PATENT DOCUMENTS

| | | |
|---|---|---|
| WO | 2003054523 A2 | 7/2003 |
| WO | 2005010542 A2 | 2/2005 |

(Continued)

OTHER PUBLICATIONS

Luxton, Richard et al "Use of External Magnetic Fields to Reduce Reaction Times in an Immunoassay using Micrometer-Sized Paramagnetic Particles as Labels (Magnetoimmunoassay)" Anal. Chem. 2004, vol. 76, pp. 1715-1719.

*Primary Examiner* — Melanie Brown
(74) *Attorney, Agent, or Firm* — McCoy Russell LLP (57) ABSTRACT

A method for controlling the movement of magnetic or magnetizable objects (10) in a biosensor cartridge. The method comprises the step of providing a biosensor cartridge with a laterally extending sensor surface (A) and at least a magnetic field generating means (20, 30, 30') for generating a magnetic field with a field gradient substantially perpendicular to the sensor surface (A). The magnetic field generating means (20, 30, 30') are alternatingly actuated such that the generated magnetic field directs alternatingly the magnetic or magnetizable objects (10) substantially perpendicular to the sensor surface (A) away and toward the sensor surface, wherein pulse lengths of the alternating actuation are adjusted such that a lateral movement of magnetizable objects along the laterally extending sensor surface is substantially avoided.

17 Claims, 6 Drawing Sheets

(51) Int. Cl.
  *B03C 1/28* (2006.01)
  *G01N 27/74* (2006.01)
  *B01L 3/00* (2006.01)
  *G01R 33/12* (2006.01)

(52) U.S. Cl.
  CPC ........... *B03C 5/028* (2013.01); *G01N 27/745* (2013.01); *G01R 33/1269* (2013.01); *B01L 2200/0668* (2013.01); *B01L 2400/043* (2013.01); *B03C 2201/18* (2013.01)

(58) Field of Classification Search
  CPC .. G01N 33/54333; G01N 27/745; A61B 5/05; B03C 5/028; B03C 1/288; B01L 3/502761; G01R 33/1269
  USPC .................................................. 436/526, 518
  See application file for complete search history.

(56) References Cited

U.S. PATENT DOCUMENTS

| | | | |
|---|---|---|---|
| 2005/0106758 A1 | 5/2005 | Fukumoto | |
| 2005/0237139 A1* | 10/2005 | Marioni | 335/220 |
| 2007/0042506 A1* | 2/2007 | Bangert | G01N 33/54333 436/518 |
| 2008/0160622 A1* | 7/2008 | Su et al. | 436/86 |
| 2008/0206104 A1* | 8/2008 | Prins | G01N 27/745 422/82.01 |
| 2010/0289483 A1* | 11/2010 | Immink et al. | 324/204 |
| 2010/0324828 A1* | 12/2010 | Kahlman | B82Y 25/00 702/19 |

FOREIGN PATENT DOCUMENTS

| | | |
|---|---|---|
| WO | 2005010543 A1 | 2/2005 |
| WO | 2005111596 A1 | 11/2005 |
| WO | 2006134546 A2 | 12/2006 |
| WO | 2007129275 A2 | 11/2007 |
| WO | 2007129277 A2 | 11/2007 |
| WO | 2007129284 A1 | 11/2007 |
| WO | 2008010110 A1 | 1/2008 |
| WO | 2008102218 A1 | 8/2008 |

* cited by examiner

PULSED MAGNETIC ACTUATION FOR SENSITIVE ASSAYS

FIELD OF THE INVENTION

The present invention relates to method for controlling the magnetic field for a pulsed magnetic actuation and for detection of magnetic or magnetizable objects in a biosensor system. The present invention also relates to a biosensor system with at least two magnetic field generating means for the pulsed actuation of magnetic particles in a biosensor systems, the controlled movement of magnetic or magnetizable objects and the detection of magnetic or magnetizable objects in a cartridge of a biosensor system.

BACKGROUND OF THE INVENTION

Various analytical procedures to detect an analyte in a test sample are known. For example, immunoassays use the mechanisms of the immune system, wherein antibodies and the respective antigens are capable of binding to one another. This specific reaction mechanism is used to determine the presence or concentration of the antigen in a test sample. In particular, the antibody or the antigen (analyte of interest) is labeled to quantify the interactions between antibody and antigen. Common labels are, for example, fluorescent and chemiluminescent molecules, colored particles (beads) or radioisotopes.

Recently, magnetic labels have been used in immunoassays to detect the presence or quantity of an analyte. The use of magnetic labels as, for example magnetic particles (beads), has several advantages. The magnetic particles can be actuated by applying a magnetic field such that the analytical procedure can be accelerated. Further, there is no magnetic background signal in a biological test sample influencing the detection of the magnetic particles.

However, these immunoassays using magnetic labels require means for (a) actuating the magnetic particles bound to the antigens to be immobilized near the sensor surface of the sensor cartridge, and for (b) flushing away the remaining unbound magnetic particles not to influence the quantity measurement of the bound particles. Therefore, for example, two magnets may be arranged on opposite sides of the sensor cartridge, wherein the first magnet attracts the magnetic particles to move through the test sample toward the sensor surface, and then the second magnet attracts unbound magnetic particles to move away from the sensor surface. In this configuration, the two magnets are mounted on a holding structure, and the holding structure mechanically moves the magnets toward or away from the sensor surface (see R. Luxton et al., "Use of External Magnetic Fields to reduce reaction times in an immunoassay . . . ", Anal. Chem. 2004, 76, 1715-1719).

Such a method is very laborious and time-consuming and needs a complex support system for arranging the two magnets on opposite sides of the sensor cartridge. A further, more efficient way of actuating magnetic particles is by using pulsed actuation my means of a plurality of magnets arranged around the sensor cartridge. In this way, the particles can be repeatedly brought in contact with the sensor surface where a biological bond can be formed. The movement away from the sensor surface is often referred to as "washing step". When actuating the particles, the bound particles are typically constantly subjected to magnetic forces, but may be also subjected to mechanical forces when other (unbound) particles come in contact with the bound particles. If these forces are too large and one bond is broken, the signal is lost and the sensitivity of the assay decreases. In other words, in biosensors using actuated magnetic particles, the bonds that keep a particle bound to the sensor surface can be disrupted again as a result of too harsh actuation.

Moreover, after the actuation or binding step usually a magnetic washing step is incorporated to remove unbound particles from the sensor surface. The bound particles are then detected using a technique that is sensitive only to particles that are close to the surface (detection area). However, it has been noted that a stable end signal is often not observed after such a washing step.

The inventors of the present invention studied and discovered mechanisms, which cause such a decreased sensitivity of the assay and the unstable signal after the washing step. In the following possible mechanisms will be discussed in more detail.

Figure 1:
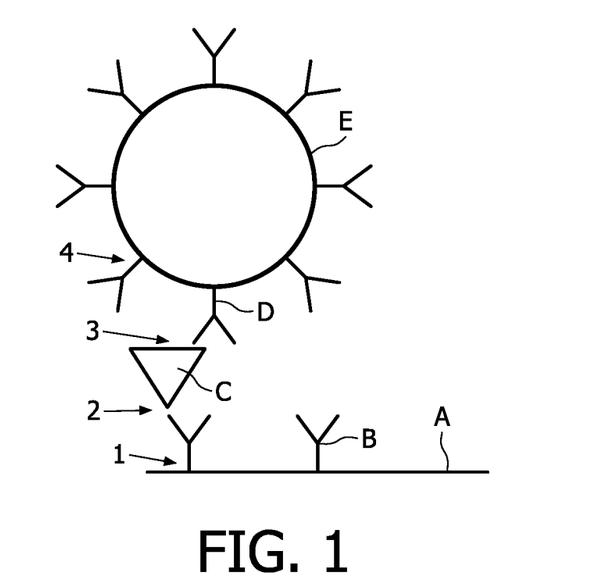
FIG. 1 schematically shows a plurality of bonds that are formed in a typical sandwich immunoassay.

In a typical biological assay, there can be several bonds that keep a particle bound to the sensor surface, shown for a sandwich immunoassay in FIG. 1. In particular, the magnetic particle E is bound to the sensor surface A through the primary antibody B, the analyte or target molecule C and the secondary antibody D. The bonds between the different parts are indicated with numbers, namely the bond between the sensor surface A and the primary antibody B is labeled by 1; the bond between the primary antibody B and the target molecule C is labeled by 2; the bond between the target molecule C and the secondary antibody D is labeled by 3 and the bond between the secondary antibody D and the particle E is labeled by 4.

The magnetic particle E is actuated to a sensor surface, by means of an external magnetic force. In order to bind the particle E to the sensor surface A, a plurality of bonds is needed. During actuation, however, the forces that are exerted on the particles can be too large to keep the particles bound to the surface, which finally results in a lower signal. Especially the non-covalent bonds are susceptible to disruption if enough force is exerted on the particle. It has been found that the disruption of the bond(s) is often irreversible, resulting in less functionality of the particle or the sensor surface, ultimately leading to a decreased sensitivity of the assay. AFM analyses of damaged areas have shown that even the primary antibody B can be removed during actuation. Therefore, this problem arises in particular in assays where a biological molecule is bound to the sensor surface by relatively weak interactions, as is the case with physisorbed antibody on a plastic (e.g. polystyrene) surface.

In addition, the degree of signal loss due to this phenomenon is dependent on the amount of already bound particles. In particular, particles that are 'protected' by the presence of nearby bound particles are more difficult to remove.

The inventors of the present invention further noted that the signal during or after the magnetic washing step is often not very stable. Such an unstable signal introduces a further error in the amount of detected analyte, further reducing the accuracy and the sensitivity of the assay.

Figure 6A:
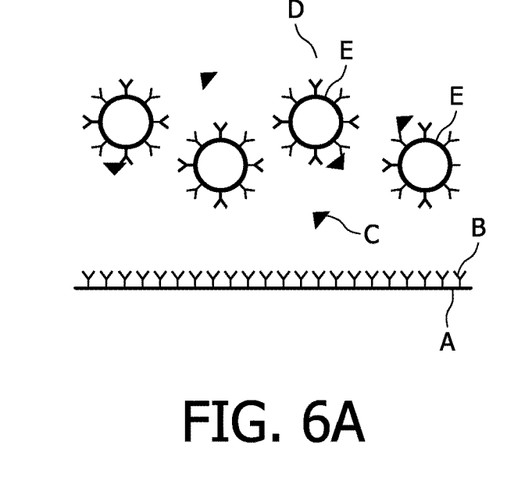
FIG. 6A schematically shows an immunoassay in solution.
Figure 6B:
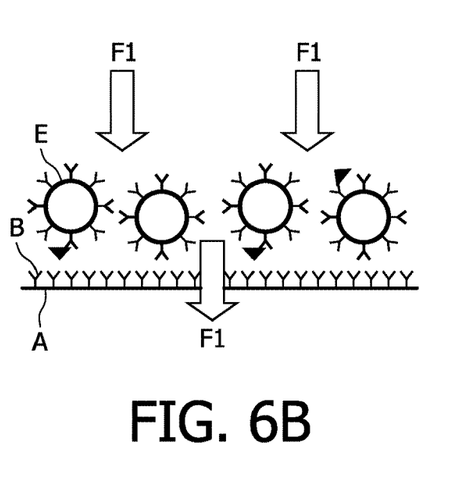
FIG. 6B schematically shows the immunoassay of FIG. 3A during an actuation step.
Figure 6C:
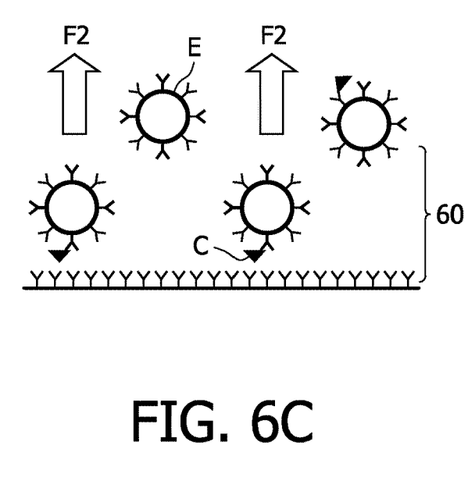
FIG. 6C schematically shows the immunoassay of FIG. 3A during a washing step.

FIGS. 6A to 6C show different steps of a typical assay in a biosensor. In particular, FIG. 6A shows the magnetic particles E which can bind to the analyte or target molecule C in solution. In order to bind the particles E with bound target molecules C to the sensor surface A, a magnetic field is applied such that the particles E travel to the sensor surface (see FIG. 6B). The force F1 of the magnetic filed which acts on the particles E is indicated by the double arrows in FIG. 6B. The unbound particles are magnetically removed from the sensor surface in a subsequent washing step (see FIG. 6C). Again, the force F2 of the magnetic field which acts on the particles E is indicated by the double arrows in FIG. 6C. In a subsequent step the bound particles are detected using a technique that is sensitive only to particles that are close to the sensor surface A.

The inventors of the present invention discovered that the instability of the signal after the washing step (see FIG. 6B) is substantially caused by sedimentation of non-bound particles, especially when relatively large particles are used (e.g. particles with a diameter of 500 nm are frequently used in these biosensors). This mechanism will be explained with reference to FIGS. 7A, 7B and 8.

Figure 7A:
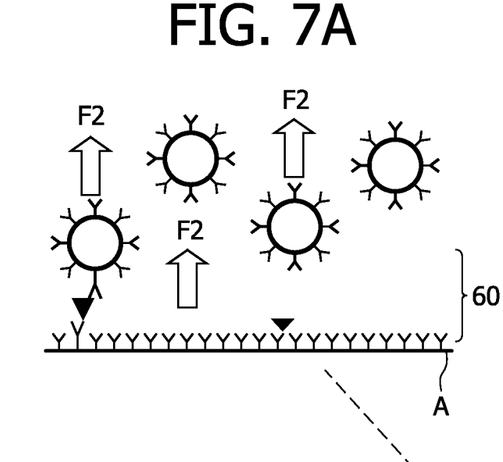
FIGS. 7A and 7B schematically show an immunoassay during a washing an a sedimentation step, respectively.

FIG. 7A is similar to FIG. 6C, which illustrates the washing step.

Figure 7B:
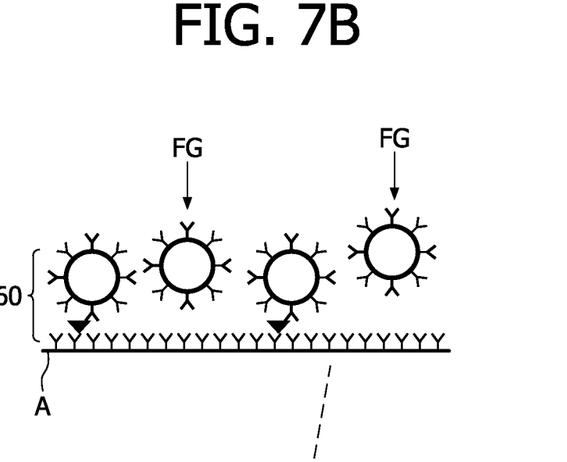

When the magnetic field of the washing step is switched off for detecting the bound particles, sedimenting particles can re-enter the detection area 60 close to the surface A as illustrated in FIG. 7B. In particular, the gravitational force which causes the particles to travel down to the sensor surface A is indicated by the single arrows FG.

Figure 8:
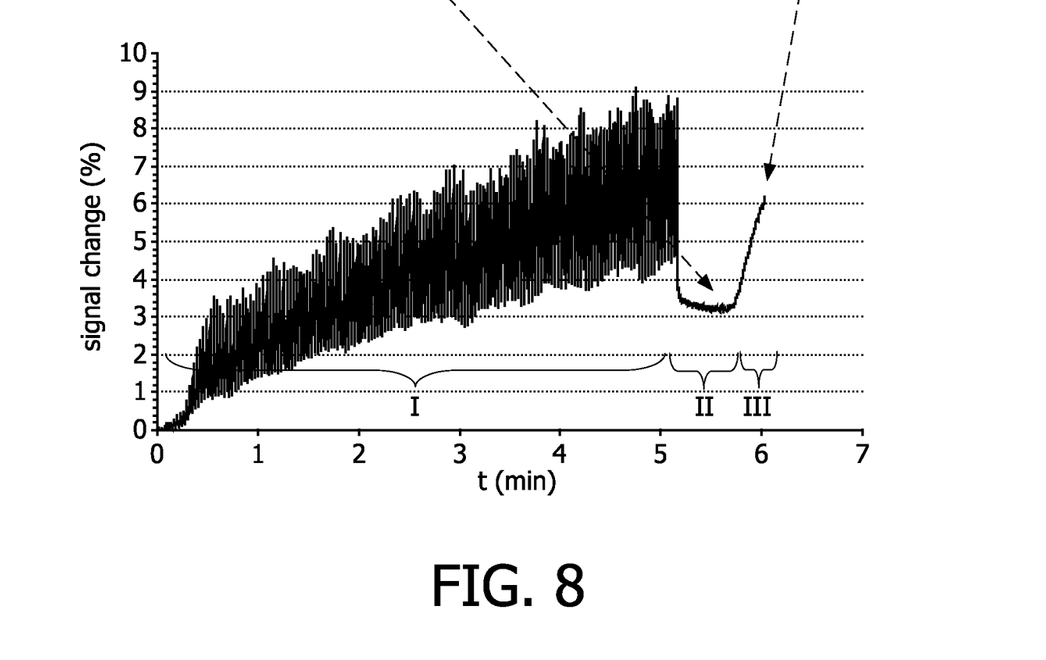
FIG. 8 shows a diagram with the signal change during an activation and washing step in a conventional system.

FIG. 8 shows the signal change in the three regimes of (I) magnetic attraction, i.e., the actuation step; (II) magnetic removing, i.e., the washing step; and (III) after switching of the magnetic field of the washing step, i.e., the detecting step. As can be clearly seen in the regime III of FIG. 8, sedimeted particles re-entering the detection area 60 are additionally detected which results in a signal increase. Instead of collecting the signal after the washing step, the signal may be collected during the magnetic washing step itself (see regime II in FIG. 8). However, as can be seen, this signal is also unstable as unbound particles are constantly being removed from the detection area 60. Furthermore, the forces applied during a washing step also act on the bound particles and can move the particle further away from the surface or even disrupt the biological bond, resulting in a signal decrease. Especially in assays where a very low signal is obtained, close to the instrumental noise, the signal to noise ratio (S/N) has to be improved by averaging the signal over a longer period. It is then important that the signal is stable in time. Especially for those assays, an unstable signal will decrease the sensitivity of the assay.

SUMMARY OF THE INVENTION

There is therefore a need to provide a system and a method which avoids the above discussed decrease of sensitivity. In particular, there is a need for a system and a method which minimizes the above described undesired removal or accumulation of particles at the sensor surface. In particular, surface damages should be avoided in very sensitive assays where only a low number of particles will bind to the sensor surface, and a timely stable signal is required for the detection.

A solution to the above-identified problem is achieved by actuating and washing the particles in a manner in which any undesired movement of particles in detection area next to the sensor surface is avoided. In particular, parallel particle movement in the detection area next to the sensor surface is minimized or avoided such that already bond particles or antibodies bond to the sensor surface are not removed.

In the context of this invention, in particular the claims, it is noted that the terms "magnetic object" or "magnetizable object" relates to any type of objects, like particle, particles, beads and/or microparticles, particularly microbeads, nanoparticles or molecules, particularly biomolecules, proteins and other biopolymers as well as biological cells or subcellular fragments, viral particles or viruses and cellular organelles and the like or inorganic compounds which are either magnetic and/or magnetizable or bound to a magnetic and/or magnetizable particle. Moreover, in the context of the invention, the terms magnetic field generating means relates to any means for generating a magnetic files such as "electromagnet", "magnetic coil" or "electromagnetic unit" etc. The terms "area of interest" or "detection area" of the sensor refers in the context of the invention to the location next to the sensor surface, where the particles are detected during the detection step.

According to a first aspect, the present invention relates to a method for controlling the movement of magnetic or magnetizable objects in a biosensor cartridge. The method comprises the following steps. A biosensor cartridge with a laterally extending sensor surface and at least a magnetic field generating means for generating a magnetic field with a field gradient perpendicular or substantially perpendicular to the sensor surface are provided. The magnetic field generating means are preferably alternatingly actuated such that the generated magnetic field directs alternatingly the magnetic or magnetizable objects perpendicular or substantially perpendicular to the sensor surface away and toward the sensor surface. The pulse lengths and the magnetic field strengths during the alternatingly actuation and washing are preferably adjusted such that a lateral movement of magnetizable objects along the laterally extending sensor surface is substantially avoided.

According to a further aspect of the invention, the pulse length and the magnetic field strength during the detection of the particles in the detection area are preferably adjusted such the concentration of particles in the detection area is preferably constant, i.e., a substantial depletion of accumulation of particles in the detection area next to the sensor surface is may be avoided by adjusting the magnetic field, such that any movement of the particles in the detection area is avoided. Such an adjusted magnetic field is preferably provided in a detection pulse, preferably after the actuation and washing step.

In other word, the method according to the present invention preferably comprise the step of adjusting the magnetic field for a certain duration of time such that the absolute value of the force acting on the magnetic or magnetizable objects opposite to the direction of the gravitational force is equal or larger then the absolute value of the gravitational force. Still in other words, the resulting force of the magnetic field acting against the gravitational force is adjusted such that the magnetic or magnetizable objects remain substantially stationary within the solution.

The magnetic field generating means or the electromagnets are preferably arranged either only on one side of the laterally extending sensor surface or on substantially opposite sites of a laterally extending sensor surface of the biosensor. It is further preferred that the electromagnets create a magnetic field gradient perpendicular or substantially perpendicular to the sensor surface. The generated magnetic field is preferably inhomogenous in the direction perpendicular or substantially perpendicular to the sensor surface. In particular, the magnetic field is preferably created such that induced lateral forces along (parallel to) the sensor surface are avoided. In other words, the electromagnet(s) is/are preferably constructed, arranged and actuated such that in the vicinity of the surface of the biosensor lateral components of a magnetic field gradient are minimized or avoided.

However, in case there is a (very) small lateral magnetic field gradient created the particles will be caused to move to or assemble also in a lateral direction. Such minimal lateral gradients may be induced due to misalignment of magnet coils or even some magnetic beads can introduce local magnetic field gradients parallel to the sensor surface. The most common cause for a lateral component, however, is because of the limited geometry of the magnets. As long as the size of the magnet is more or less comparable to the size of the area of interest on the biosensor surface, the field is inhomogeneous. In other words, beads are attracted towards the magnet center. At such a point, there will be some lateral component created which are very small, i.e., even if the induced movement is substantially perpendicular toward and away the sensor surface, the (small) lateral magnetic field gradient results in a diagonal movement of the particles (summation of the lateral and perpendicular force vector).

The inventors of the present invention discovered that an alternating actuation of the magnetic coils avoids a surface damage although small and/or accidentally created lateral forces of the magnetic field may cause a lateral movement of the particles. Thus, according to the present invention, the magnetic field generating means (e.g. electromagnets) are alternatingly actuated such that a damage of the sensor surface is substantially avoided, although there may be (small) lateral magnetic field gradients present.

The magnetic field generating means according to the present invention may be at least one electromagnet, preferably with magnet coils. Preferably at least one, preferably two or more electromagnets may be arranged below the sensor surface. In addition to the at least one electromagnet below the sensor surface, there may be at least one electromagnet arranged above the sensor surface. Preferably each electromagnet is separately controllable by a driving means.

Preferably, two electromagnets may be arranged below the sensor surface with a slit between the two electromagnets. A single electromagnet is preferably arranged on the other side of the sensor surface opposite to said slit. The preferably two electromagnets below the sensor surface may comprise the same polarity (north-north or south-south) when actuated simultaneously for directing the particles away from the sensor surface. The at least two electromagnets preferably comprise opposite polarities (north-south or south-north) when actuated simultaneously for inducing a particle movement toward the sensor surface, i.e. for attracting the particles to the sensor surface.

On the other hand, the preferably one electromagnetic above the surface is preferably actuated for inducing a particle movement away from the surface. The movement away from the surface is often referred to as "washing step". In particular, traditional washing steps based on the flow of liquid over the sensor surface can be replaced by magnetic washing steps, where the unbound particles can be pulled from the surface with a magnetic field.

Figure 4:
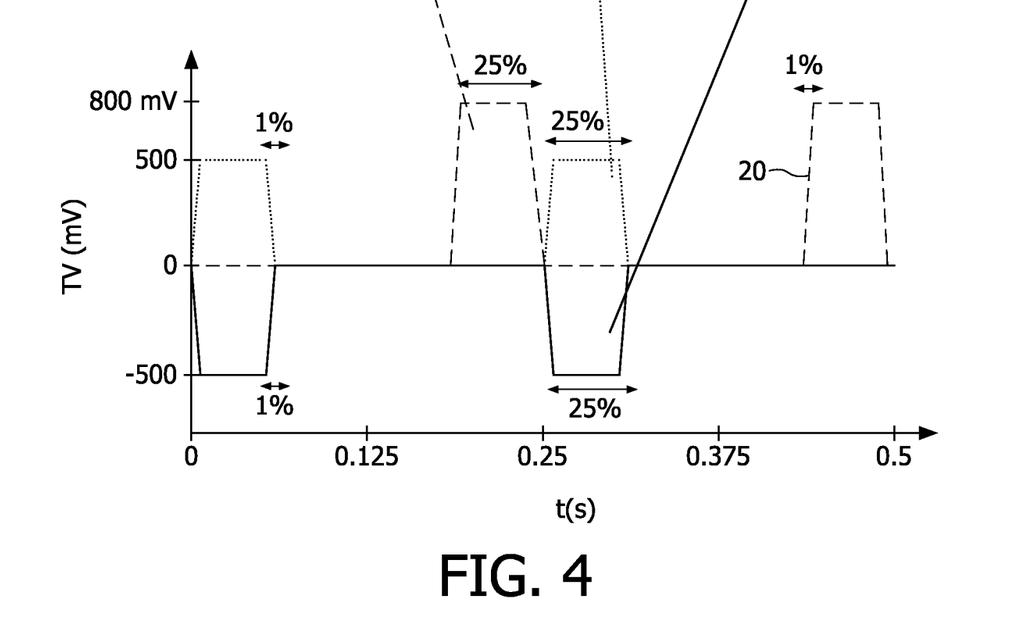
FIG. 4. shows the actuating voltages dependent on the time for controlling the three magnetic coils of the embodiment shown in FIGS. 4A and 4B.

The alternating or periodically actuation of the electromagnets will be further specified wherein it is sufficient to refer to only a single period of an actuation cycle (see e.g. FIG. 4). Preferably, a period of the alternating actuation comprises a first pulse length for directing the magnetic or magnetizable objects toward the sensor surface. In a subsequent step a second pulse length for directing the magnetic or magnetizable objects away from the sensor surface may be generated. According to a preferred embodiment of the present invention, there is a time interval between the first pulse length and the second pulse length with substantially no generated magnetic field. In other words, there may be a short "off-time" after the first and/or second magnetic pulse length. Preferably the "off-time" is adjusted to the specific requirements of the system. In particular, the off-time is adjusted such that it corresponds to the diffusion or sedimentation time needed for the particle to reach the surface. In other words, the pulse for directing the particles toward the sensor surface is preferably succeeded by a short "off-time" tailored to the specific situation, i.e. the distance that has to be spanned and the size of the used particles.

According to a preferred embodiment of the present invention, the step for directing the particles away from the sensor surface (e.g. actuated top magnet) may not be performed directly after the actuated magnetic field for directing the particles toward the sensor surface (e.g. actuated bottom magnets). In particular, it is preferred that all electromagnets are switched off after the bottom magnets have been switched on. Thus, there may exists a time interval between the actuation of the bottom electromagnets and the actuation of the top magnet without generated magnetic field. This time interval provides the advantage that the particles are allowed to diffuse or sediment to the sensor surface.

According to a further preferred embodiment of the present invention the generated magnetic field after a washing step is adjusted such that a change of the particle concentration in the detection area next to the sensor surface is avoided. In particular, magnetic field is preferably adjusted such that the particles are held in an equilibrium state, e.g., the gravitational force pulling the particles toward the sensor surface is substantially compensated or compensated by the magnetic field acting substantially into the opposite direction to the gravitational force, such that the distance of each particle to the sensor surface is substantially held constant.

In other words, the method according to the present invention may comprise a detection pulse during which the magnetic field is adjusted such that the absolute value of the force acting on the magnetic or magnetizable objects opposite to the direction of the gravitational force is equal or larger than the absolute value of the gravitational force. Still in other words, the magnetic field is adjusted such that the movement of the magnetic or magnetizable objects toward the sensor surface is avoided. According to a preferred embodiment, the movement of the magnetic or magnetizable objects toward and away from the sensor surface is avoided.

In particular, the height of the current used to generate the magnetic field is preferably chosen such that the gravitational force acting on the particles can just be overcome. In this manner, substantially no sedimentation of particles will be observed. Furthermore, the force acting on the particles will be minimal, so no specific bonds of the sensor surface will be broken. Such an adjustment of the magnetic field is preferably applied during a signal determination or measurement step. As a result, the signal will be very stable and can then be averaged over a sufficient time span to increase the S/N. In addition, because the signal is collected in a well-defined separate step, signal processing becomes very straightforward.

The frequency of the alternating modulation is preferably larger than 1 Hz and preferably lower than 10 Hz, more preferably larger than 2 Hz and lower than 6 Hz and more preferably between 3 and 5 Hz and yet preferably about 4 Hz. However, depending on the size of the particles and the flow resistance of the particles within the solution the particular configuration of the magnets, and/or the particular particle concentration etc., the frequency of the alternating modulation may be different from the above suggested ranges. The voltage applied to the magnetic coils may comprise a rectangle pattern or a trapezoid pattern.

For instance, using the above mentioned frequencies, the time interval between the first pulse length and the second pulse length may be more than 30% of a period, preferably more than 40% and more preferably 50%. At a frequency of 4 Hz, the 50% off time amounts to 125 ms, which is advantageously for magnet/biosensor configuration as described and depicted in the detailed description with 500 nm beads.

The first pulse length with the first generated magnetic field strength and the second pulse length with the second generated magnetic field strength may be further adjusted such that the magnetic or magnetizable objects are directed approximately the same distance during the phases of movements away the sensor surface and toward the sensor surface. The first and/or second pulse length may be at least 5% of a period, preferably at least 20%, more preferably approximately 25% and preferably less than 40%.

In other words, a duty cycle (the pulse length or time interval of an actuated electromagnet within a period) for directing the magnetic or magnetizable objects away from the sensor surface is preferably between 10 and 40% and more preferably about 25% of a whole period. However, as will be recognized by a person skilled in the art, this preferred pulse length is dependent on the particular configuration of the magnets, a particular particle size, a particular particle concentration concentration, etc. It is further preferred that a single period comprises only one duty cycle for directing the magnetic or magnetizable objects away from the sensor surface. It is further preferred that a single period (also called first pulse length in the following) comprises only one duty cycle for directing the magnetic or magnetizable objects toward the sensor surface. It is further preferred that a single period comprises only one duty cycle (also called second pulse length in the following) for directing the magnetic or magnetizable objects away from the sensor surface. Moreover, it is further preferred that there exists a time interval during a period in which none of the electromagnets is actuated. In particular, it is preferred that such a "off-time" time interval is after the first pulse length and before the second pulse length.

According to the method of the present invention, any magnetic or magnetizable objects, which are located at or next to the sensor surface, preferably move firstly a predetermined distance away from the surface and subsequently move substantially a smaller or the same predetermined distance toward the surface during a period of the alternating actuation.

Accordingly, the duty cycle for directing the magnetic or magnetizable objects toward the sensor surface is also preferably between 10 and 40% and more preferably about 25% of a whole period. It is further preferred that a period comprises only one duty cycle for directing the magnetic or magnetizable objects toward the sensor surface. The duration of a duty cycle (pulse length) for inducing a movement away and toward the surface may be equal. However, since the distance travelled by the particles is dependent on the pulse length and the amplitude of the pulse, the pulse length may be chosen shorter by higher amplitudes and vice versa.

The present invention also relates to a biosensor system for conducting the above preferred method steps. The biosensor system preferably comprises a detachably or fixed arranged biosensor cartridge with a laterally extending sensor surface and at least a magnetic field generating means for generating a magnetic field with a field gradient substantially perpendicular to the sensor surface. The system may further comprise a driving unit for alternatingly actuating the magnetic field generating means such that generated magnetic field directs alternatingly the magnetic or magnetizable objects perpendicular or substantially perpendicular to the sensor surface away and toward the sensor surface. The driving unit is preferably adapted for generating pulse lengths of the alternating actuation which avoids a lateral movement of magnetizable objects along the sensor surface.

In particular, the driving unit is preferably adapted to actuate at least two electromagnets being arranged below the sensor surface simultaneously with opposite polarities in order to direct the magnetizable objects toward the sensor surface and/or to actuated the at least two electromagnets simultaneously with same polarities in order to direct the magnetizable objects away from the sensor surface. The created, preferably inhomogenic magnetic field with large perpendicular and minimized but possibly small or very small parallel gradient cause that any magnetic or magnetizable object/particle which is located next to the sensor surface moves substantially in a direction perpendicular to the sensor surface, whereas the movement parallel to the sensor surface is minimized or avoided.

The system of the present invention, in particular the driving unit is preferably adapted for controlling the movement of magnetic or magnetizable particles/objects (and therefore the actuation) in a biosensor cartridge. The driving unit is preferably adapted to actuate the electromagnets alternatingly (alternatingly switching on and/or off) such that the induced direction of movement of any magnetic or magnetizable object/particle, which is located preferably next to the sensor surface, comprises mainly a component perpendicular to the laterally extending sensor surface when the objects are directed away and/or toward the sensor surface. In other words, it is preferred that simultaneously with the particle movement away and toward the surface a lateral movement due to a possibly generated lateral field component is avoided or minimized. The velocity vector of magnetic or magnetizable object/particle is preferably built by components parallel (lateral) and perpendicular to the sensor surface when the particles are directed to or away from the sensor surface, wherein the perpendicular component is substantially larger than the lateral component. Preferably the lateral component is zero. In this way, the particles can be repeatedly brought in contact with the sensor surface where a biological bond can be formed without removing already bond particles from the surface.

Preferably, the electromagnet(s) above the sensor surface is/are switched off when the electromagnet(s) below the surface is/are actuated and vice versa. In other words, it is preferred that the actuation of the above and the below magnet coils are modulated in an alternating manner. However, according to a further aspect of the invention, the individual actuation phases of the individual magnets may overlap. In particular, simultaneously with the actuation of the lower magnet coils, the field of the upper coil may be reduced instead of totally switched off and vice versa.

According to a further preferred embodiment according to the present invention the driving unit is adapted to generate magnetic field strengths and/or the duration of the magnetic fields such that the magnetic or magnetizable objects travel approximately the same distance during the two phases of movements away from the sensor surface and toward the sensor surface. For instance, a particle which is located next or in the vicinity to the sensor surface (but preferably not bound to the surface) is directed away from the sensor surface by a predetermined distance, e.g. due to the field created by the upper electromagnet. In other words, the non-bound particles are removed from the sensor surface by a magnetic washing step. This predetermined distance may be controlled by the generated field strength, e.g. the voltage which is applied to the coils of the electromagnet, and/or the pulse length (duration) of the generated magnetic field. The velocity vector of the away directed particle preferably comprises components perpendicular and optionally parallel to the sensor surface. For directing the same particle back toward the surface (e.g. for bonding), the magnetic field, in particular the field strength and the pulse length (duration) is preferably generated such that the particle travels the same amount of distance back. In particular, it is preferred that the travel distance perpendicular to the sensor surface during an induced movement away is substantially the same like the travel distance perpendicular to the sensor surface during an induced movement toward the sensor surface. In other words, it may be possible that the travel distance lateral along the sensor surface is different during the induced particle movements away and toward the sensor surface.

These and other aspects of the invention will be apparent from and elucidated with reference to the embodiments described hereafter.

DETAILED DESCRIPTION OF EMBODIMENTS

The inventors of the present invention identified the presence of lateral forces (parallel to the sensor surface), acting on particles that are close to the sensor surface as one of the main contributors of the above described problem. Compared to forces perpendicular to the sensor surface, these lateral forces can probably induce much higher forces on the biological bonds through the large torque that is created.

Figure 2:
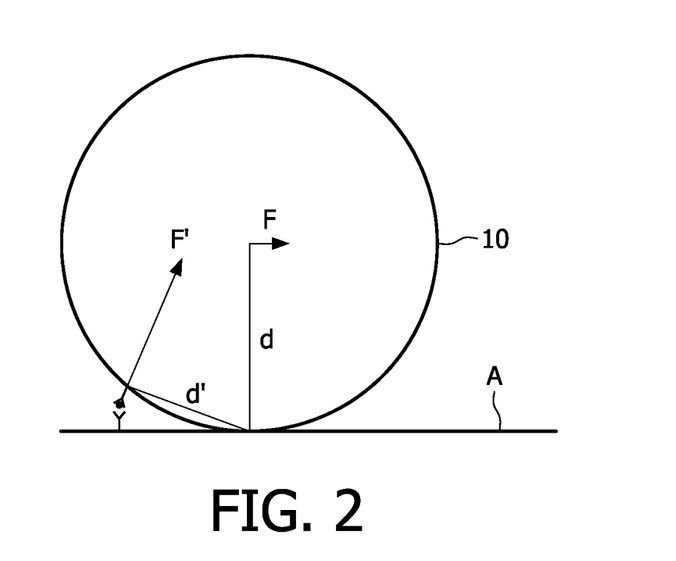
FIG. 2 schematically illustrates the lateral forces that may be applied to a bond particle during actuation.

In particular, FIG. 2 illustrates how a relatively small force F, parallel (lateral) to the sensor surface, can induce a relatively larger force on a biological bond due to the long arm "d" created by the relatively large size of the magnetic particle 10. The resulting force, which acts on the bond between the particle and the bond is indicated by F' which is significantly larger than the parallel force F. Moreover, the inventors of the present invention also observed that single unbound particles can be dragged over the sensor surface and remove already bound particles in its path. A solution to this problem is to actuate the particles in a manner in which the lateral movement of the particles near the surface is minimized or avoided.

Figure 3A:
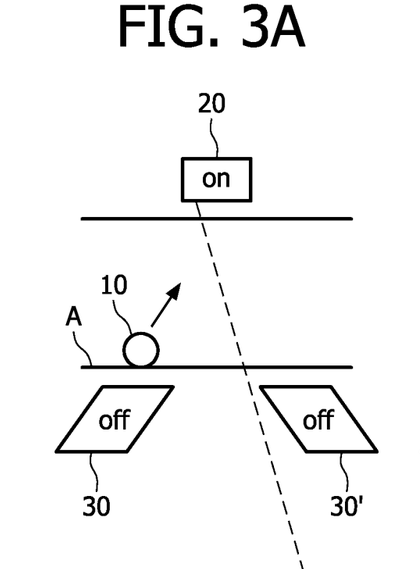
FIGS. 3A and 3B schematically shows a set-up for a biosensor system according to the present invention with one magnetic coil above a biosensor cartridge and two magnetic coils below the biosensor cartridge.
Figure 3B:
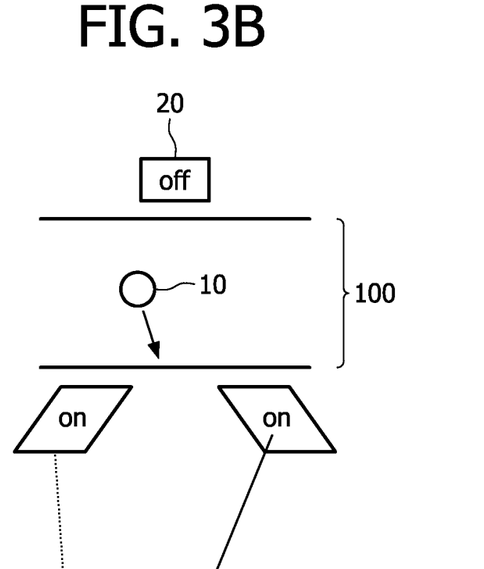

FIGS. 3A and 3B show a particular configuration according to the present invention with external magnets or magnetic coils, namely bottom and top magnets which are arranged on substantially opposite sides below and above the sensor surface, respectively, that are used for actuation. In particular, two magnetic coils 30, 30' (bottom magnets) are arranged below the sensor surface "A". A biosensor cartridge with a laterally extending sensor surface A is arranged between the magnetic coils (only partly shown). In particular, the sensor cartridge is preferably filled with a liquid which comprises the magnetic or magnetizable particles 10, e.g. paramagnetic particles 10, which may be bound by one or a plurality bounds (see FIG. 1) to the sensor surface A. To increase the actuation of particles, the magnetic actuation coils 30, 30' are arranged below the sensor surface A to generate a magnetic field to pull the particle 1 towards the sensor surface A. As shown in FIG. 3B, a pair of coils 30, 30' may be used. However, it is equally possible to only use one magnetic coil below the sensor surface A. After a predetermined time, the lower coils 30, 30' are switched off such that no magnetic field is present at the cartridge.

Another magnetic field generated by a magnetic coil 20 arranged above the sensor surface A may be applied to pull the non-bonded particles away from the sensor surface A (FIG. 4A). As can be seen in FIG. 4, the upper magnetic coil 20 is not actuated immediately after switching off the lower coils. It is preferred that a time interval with out generated magnetic filed is provided before the actuation of the upper magnetic coil 20. In more detail, a short "off-time" of the magnet directly after the attraction pulse, long enough to allow the particles to diffuse to the sensor surface where a bond can be formed is preferred.

After the particles are again directed away from the sensor surface by means of the upper coil 2, the upper coil 2 is subsequently switched off and the lower coils (30,30') are switched on again (see FIG. 4B), and so on.

This toward and away directed movement is induced by magnetic field gradients which are directed substantially perpendicular to the surface A. However, small or very small magnetic field gradients parallel to the surface may be created due to the size or the alignment of the magnets. As discussed above with regard to FIG. 3, already very small lateral forces may remove already bound particles. To avoid a removal of already bound particles and/or a damage of the sensor surface, the magnets below and above the sensor surface are actuated alternatingly as described in more detail with the actuation scheme in FIG. 4.

Figure 5A:
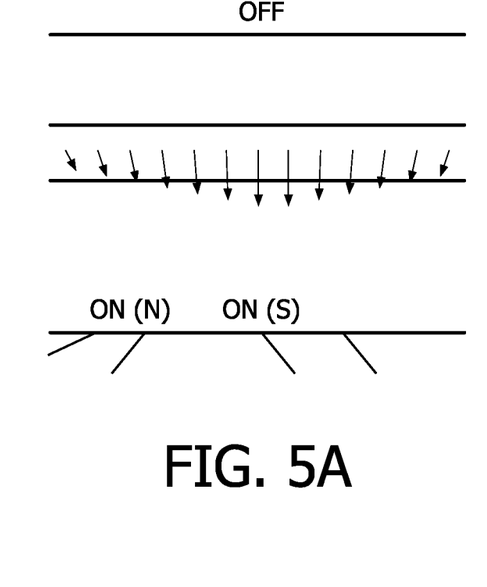
FIGS. 5A to 5C show simulations of magnetic fields in different actuation states.
Figure 5B:
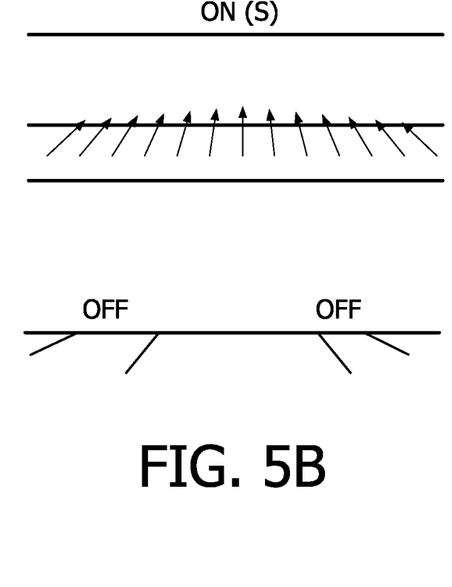
Figure 5C:
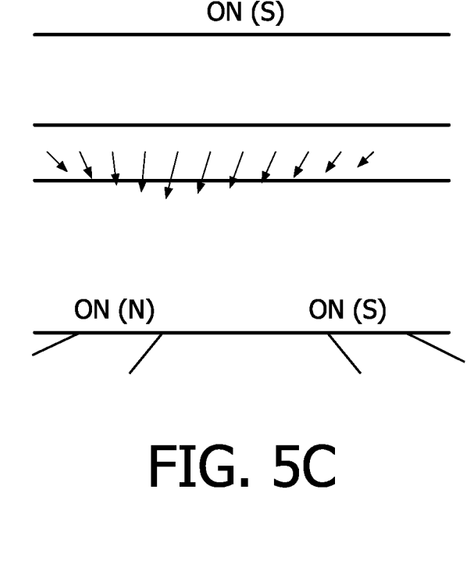

In particular, FIGS. 5A, 5B and 5C show the simulations of the magnetic fields in different states of the magnets. The strength (length of the arrow) and direction of the magnetic force acting on particles is indicated with arrows. However, it should be noted that different scales are used for the three different states. FIG. 5A shows the forces in case both bottom magnets 30, 30' are switched on (actuated) in opposite polarities, namely magnet 30 comprises the polarity north (N) whereas the magnet 30' comprises the polarity south (S). FIG. 5B shows the resulting forces when on the top magnet 20 is switched (polarity S) on and the bottom magnets 30 and 30' are not actuated. FIG. 5C shows the resulting magnetic forces when all magnets, namely the bottom magnets 30, 30' and the top magnet 20 are switched on simultaneously. The bottom magnet 30 comprises the polarity north (N) whereas the magnet 30' comprises the polarity south (S).

In order to avoid a movement of the particles lateral to the sensor surface within the detection area, the magnetic field strength of the magnetic coils are preferably controlled by a periodically voltage pattern. In particular, the applied voltages of the top and bottom coils and the pulse lengths and off-times are preferably adjusted in such a manner that the particles 10 will travel approximately the same distance during both phases, i.e., the phase away and toward the sensor surface (see FIGS. 3A and B). In this manner, the time in which the particles at the surface experience a lateral force is minimized.

As shown in FIG. 3A, the top magnet may be used to pull the particles from the surface A over a certain distance, after which the bottom magnets are switched on just long enough for the particles to reach the surface A again. Preferably, the bottom magnets 30 and 30' are only switched on for a short time such that the particles are accelerated in the direction toward the sensor surface. After switching off the bottom magnets 30, 30' the particles still diffuse during the "off-time" toward the sensor surface.

The voltage values dependent from the time for a preferred actuation pattern are exemplary shown in FIG. 4. However, as will be recognized by a person skilled in the art, the preferred pulse lengths are dependent on the particular configuration of the magnets, a particular particle size, a particular particle concentration, etc. The illustrated actuation pattern provide a gentle way of actuation, particularly advantageously in the detection of picomolar concentrations of parathyroid hormone and cardiac troponin I, but are likely applicable for other sensitive assays or assays with weak bonds as well. This actuation scheme minimizes the lateral forces and results in a considerable increase in speed and sensitivity of these assays.

In particular, alternating the use of the top 20 and bottom magnets 30, 30' according to the following method, may prevent surface damage. Magnetic or magnetizable objects/particles located at or in the vicinity of the sensor surface A are directed away from the sensor surface A. This may be achieved by actuating the top magnet 20 such that the magnetic particles are pulled away from the surface (FIG. 3A). Instead of pulling the particles away from the surface by means of the top magnet, the particles may be pushed or repelled away may means of the bottom magnets. Moreover, a combination of pulling and pushing the particles may be achieved by an appropriate actuation of the top and bottom magnetic coils. In the next step, the particles, which moved away from the sensor surface are subsequently attracted using the bottom coils just long enough that the particles 1 reach the surface A again (see FIG. 3B). Again, a combination of pushing and repelling the particles may be achieved by an appropriate actuation of the top and bottom magnetic coils.

FIG. 4 shows for example details of settings that may be used to prevent surface damage in a sandwich immunoassay for cardiac troponin I. The bottom coil 30 is operated at a pulse level of 500 mV, a frequency of 4 Hz, a duty cycle of 25% with an edge time of 1%. The other bottom coil 30' is operated in the same manner with a pulse level of −500 mV. The top coil 20 is operated using the same frequency, duty cycle and edge time, only using a pulse level of 800 mV and a phase shift of 75%. As it would be evident for a person skilled in the art, the mentioned values are dependent on the used setup (coils, three-dimensional layout etc.). In other words, the above-described embodiment with three magnetic coils is merely a preferred embodiment according to the present invention. However, the general method is applicable to other actuation schemes with other magnet configurations as well.

Figure 9:
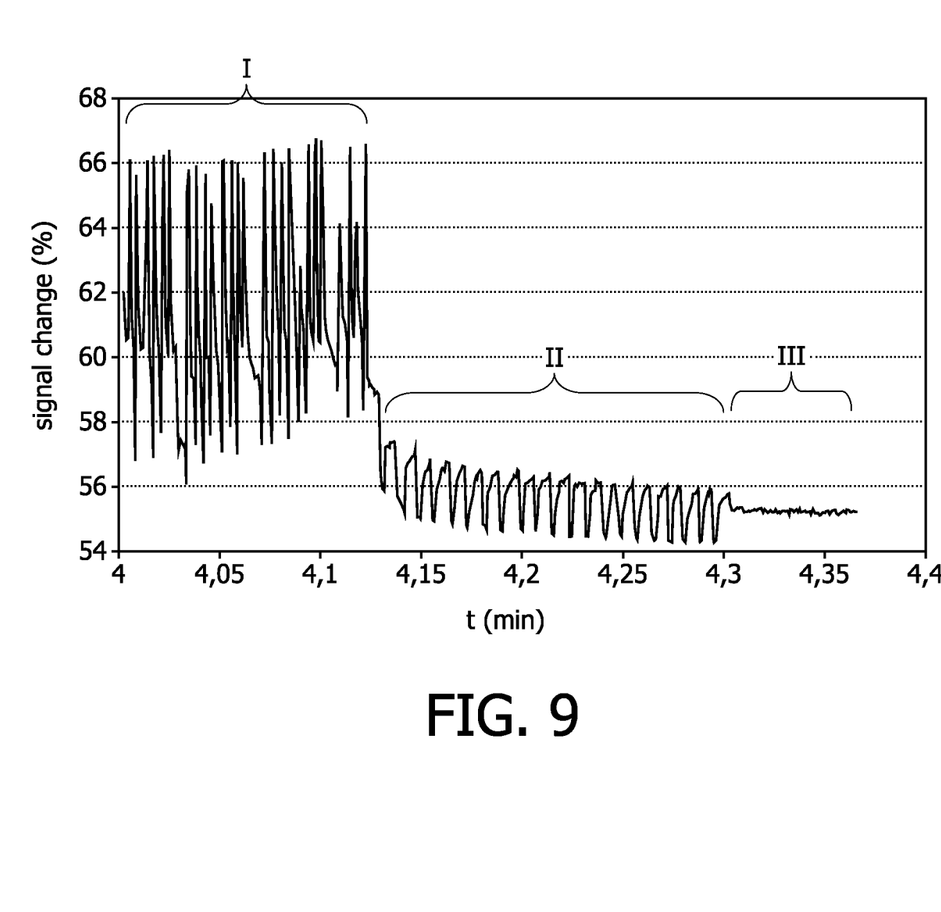
FIG. 9 shows a diagram with the signal change during an activation, washing and detecting step in a method according to the present invention.

FIG. 9 refers to a further preferred embodiment of the present invention, wherein the movement of the particles is controlled during a measurement. The diagram of FIG. 9 shows the signal change during the last part of a biosensor experiment, e.g., the last parts of the alternating actuation (regime I), the magnetic washing (regime II) and the detection of the signal (regime III). As can be seen, the signal changes significantly during the alternating actuation and the washing step (regimes I and II). For instance, the signal to noise ratio S/N (defined as the signal divided by the standard deviation) in this specific example is: S/N=77. After the washing step, a detection pulse according to the present invention is provided, namely movement of particles toward or away from the detection area of the sensor is substantially avoided. Such a detection pulse during the last step ensures a stable signal, resulting in a high S/N. For instance the ration S/N=1140 is shown in the regime III in FIG. 9. With such a detection pulse, the noise during the detection step may be reduced such that the noise is substantially equal to the instrumental noise observed in the absence of particles.

While the invention has been illustrated and described in detail in the drawings and foregoing description, such illustration and description are to be considered illustrative or exemplary and non-restrictive; the invention is thus not limited to the disclosed embodiments. Variations to the disclosed embodiments can be understood and effected by those skilled in the art and practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures can not be used to advantage. Any reference signs in the claims should not be considered as limiting the scope.

The invention claimed is:

1. A biosensor comprising:
   (a) a biosensor cartridge with a laterally extending sensor surface,
   (b) at least two electromagnets arranged below the sensor surface, wherein the laterally extending sensor surface is arranged between the at least two electromagnets;
   (c) at least one electromagnet arranged above the sensor surface, the at least one electromagnet arranged above the sensor surface configured to generate magnetic fields with a field gradient substantially perpendicular to the sensor surface, wherein the at least one electromagnet arranged above the sensor surface is arranged opposite the laterally extending sensor surface arranged between the at least two electromagnets;
   wherein the at least two electromagnets below the sensor surface and the at least one electromagnet above the sensor surface are configured to be alternately actuated to generate magnetic fields which urge alternatingly a plurality of magnetic objects substantially perpendicular to the sensor surface alternately away and toward the sensor surface, wherein pulse lengths of the alternating actuation pulses are adjusted such that a lateral movement of the plurality of magnetic objects along the laterally extending sensor surface is substantially avoided.

2. The biosensor according to claim 1, wherein during the magnetic fields that urge the plurality of magnetic objects towards the sensor surface, at least one of the plurality of magnetic objects binds to the sensor surface and the at least two electromagnets are further configured to receive a washing pulse and a detection pulse, wherein the washing pulse is configured to move at least one of the plurality of magnetic objects which is unbound away from the sensor surface.

3. A biosensor comprising:
(a) a biosensor cartridge with a laterally extending sensor surface and which contains magnetic particles,
(b) at least two electromagnets arranged below the sensor surface at an angle offset to a perpendicular of the sensor surface and configured to generate a magnetic field with a field gradient, wherein the laterally extending sensor surface is arranged between the at least two electromagnets,
wherein the at least two electromagnets are configured to (1) actuate below the sensor surface simultaneously with opposite polarities to urge a plurality of magnetic objects toward and perpendicular to the sensor surface and (2) actuate below the sensor surface simultaneously with same polarities to urge the plurality of magnetic objects perpendicularly away from the sensor surface, such that lateral movement of the plurality of magnetic objects along the laterally extending sensor surface is substantially avoided.

4. The biosensor according to claim 1, wherein a frequency of the alternating actuation pulses of the at least two electromagnets is larger than 1 Hz and lower than 10 Hz.

5. The biosensor according to claim 1, wherein the at least two electromagnets are configured to receive the alternating actuation pulses such that the plurality of magnetic objects, which are located at and unbound to the sensor surface, alternately move a predetermined distance away from the sensor surface and substantially the same predetermined distance toward the sensor surface.

6. A biosensor comprising:
(a) a biosensor cartridge including a biosensor surface configured to be disposed horizontally, the biosensor cartridge containing a plurality of magnetic particles and target molecules in a fluid;
(b) first electromagnetic coils arranged above the biosensor surface and configured to apply forces perpendicular to the biosensor surface on the plurality of magnetic particles when the biosensor cartridge is disposed on the biosensor surface;
(c) at least two second electromagnetic coils arranged below the biosensor surface and offset from a perpendicular of the biosensor surface, wherein the at least two second electromagnetic coils are arranged apart from one another along a lateral surface of the biosensor and the first electromagnetic coil is arranged opposite a gap between the at least two second electromagnetic coils;
wherein the first and second electromagnetic coils and configured to receive electrical pulses which drive the first and second electromagnetic coils cyclically to:
generate a first magnetic field pulse with a first pulse strength and length to urge the plurality of magnetic particles a distance toward and perpendicularly to the biosensor surface such that some of the plurality of magnetic particles bind to the biosensor surface forming a plurality of bound magnetic particles, wherein a remainder of the plurality of magnetic particles forms a plurality of unbound magnetic particles;
generate a second magnetic field pulse with a second pulse strength and length to urge the plurality of unbound magnetic particles to move said distance perpendicularly to and away from the biosensor surface, and
provide a time interval between the first magnetic field pulse and the second magnetic field pulse with substantially no generated magnetic field such that the plurality of unbound magnetic particles diffuse away from the biosensor surface.

7. The biosensor according to claim 6, wherein at least one of the first and second magnetic field pulses is at least 5% of a period.

8. The biosensor according to claim 6, wherein the time interval between the first magnetic field pulse and the second magnetic field pulse is more than 30% of a cycle duration.

9. A biosensor system comprising:
(a) a biosensor cartridge with a laterally extending sensor surface and containing magnetic particles in a fluid,
(b) at least first and second electromagnets arranged on substantially opposite ends of a bottom of the sensor surface, a third electromagnet arranged above the sensor surface and configured to generate magnetic fields with field gradients substantially perpendicular to the sensor surface,
wherein the at least first and second electromagnets are configured to be driven to:
generate actuation magnetic fields that move a plurality of the magnetic particles substantially perpendicular to the sensor surface toward the sensor surface, such that lateral movement of the plurality of magnetic particles along the sensor surface is avoided;
generate washing magnetic fields that move the magnetic particles perpendicular to and away from the sensor surface such that lateral movement of the plurality of magnetic particles along the sensor surface is avoided.

10. The biosensor system according to claim 9, wherein the electromagnets arranged on the bottom of the sensor surface are configured to be actuated with (1) opposite polarities simultaneously in order to direct the plurality of magnetic particles toward the sensor surface and (2) same polarities simultaneously in order to direct the plurality of magnetic particles away from the sensor surface.

11. The biosensor system according to claim 10, wherein the biosensor cartridge is detachably arranged.

12. The biosensor system according to claim 9, further including:
a fourth electromagnet disposed on a same side of the sensor surface as one of the first and second electromagnets or the third electromagnet.

13. A biosensor system comprising:
(a) a biosensor cartridge with a laterally extending sensor surface and containing magnetic particles in a fluid,
(b) at least first and second electromagnets arranged on substantially opposite ends of a bottom of the sensor surface, a third electromagnet arranged above the sensor surface and configured to generate magnetic fields with field gradients substantially perpendicular to the sensor surface, and wherein the first and second electromagnets are arranged below the sensor surface at an angle offset to a perpendicular of the sensor surface;
wherein the at least first and second electromagnets are configured to be driven to:

generate actuation magnetic fields that move a plurality of the magnetic particles substantially perpendicular to the sensor surface toward the sensor surface, such that lateral movement of the plurality of magnetic particles along the sensor surface is avoided;

generate washing magnetic fields that move the magnetic particles perpendicular to and away from the sensor surface such that lateral movement of the plurality of magnetic particles along the sensor surface is avoided;

wherein the first and second electromagnets are driven with an alternating periodic voltage pattern such that the actuation and washing magnetic fields alternately urge the plurality of magnetic particles to travel a same distance in the fluid towards and away from the sensor surface.

14. The biosensor system according to claim 13, wherein the at least first and second electromagnets are configured to receive a cyclic periodic voltage pattern and the cyclic periodic voltage pattern includes:

a first pulse length for directing the plurality of magnetic particles toward the sensor surface, a second pulse length for directing the plurality of magnetic particles away from the sensor surface, and a time interval between the first pulse length and the second pulse length with substantially no generated magnetic field.

15. The biosensor system according to claim 14, wherein at least one of the first and second pulse lengths is at least 20% of a cycle period.

16. The biosensor system according to claim 14, wherein the time interval between the first pulse length and the second pulse length is more than 40% of a cycle period.

17. The biosensor system according to claim 14, wherein the at least two electromagnets are configured to receive a frequency of the alternating actuation between 2 Hz and 6 Hz.

* * * * *